(12) United States Patent
Murphy et al.

(10) Patent No.: US 8,540,748 B2
(45) Date of Patent: Sep. 24, 2013

(54) SURGICAL INSTRUMENT WRIST

(75) Inventors: Todd E. Murphy, Palo Alto, CA (US); Margaret M. Nixon, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 616 days.

(21) Appl. No.: 12/240,575

(22) Filed: Sep. 29, 2008

(65) Prior Publication Data
US 2010/0004663 A1  Jan. 7, 2010

Related U.S. Application Data

(60) Provisional application No. 61/078,543, filed on Jul. 7, 2008.

(51) Int. Cl.
*A61B 17/00* (2006.01)

(52) U.S. Cl.
USPC ............ 606/205; 606/206; 606/207; 606/208

(58) Field of Classification Search
USPC ..................... 606/205–208, 167–170, 51, 52
See application file for complete search history.

(56) References Cited

U.S. PATENT DOCUMENTS

| | | | |
|---|---|---|---|
| 4,865,376 A | 9/1989 | Leaver et al. | |
| 5,207,114 A | 5/1993 | Salisbury, Jr. et al. | |
| 5,570,920 A | 11/1996 | Crisman et al. | |
| 5,710,870 A | 1/1998 | Ohm et al. | |
| 5,784,542 A | 7/1998 | Ohm et al. | |
| 5,797,900 A | 8/1998 | Madhani et al. | |
| 5,828,813 A | 10/1998 | Ohm | |
| 6,371,952 B1 * | 4/2002 | Madhani et al. | 606/1 |
| 6,394,998 B1 * | 5/2002 | Wallace et al. | 606/1 |
| 6,676,684 B1 * | 1/2004 | Morley et al. | 606/205 |
| 6,692,485 B1 | 2/2004 | Brock et al. | |
| 6,840,938 B1 * | 1/2005 | Morley et al. | 606/51 |
| 7,101,363 B2 | 9/2006 | Nishizawa et al. | |
| 7,316,681 B2 | 1/2008 | Madhani et al. | |
| 7,398,707 B2 | 7/2008 | Morley et al. | |
| 2004/0199147 A1 * | 10/2004 | Nishizawa et al. | 606/1 |

(Continued)

FOREIGN PATENT DOCUMENTS

JP  2006061364 A  3/2006

OTHER PUBLICATIONS

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

(Continued)

*Primary Examiner* — Gary Jackson
*Assistant Examiner* — Katrina Stransky

(57) ABSTRACT

A link is positioned to pivot at the distal end of a surgical instrument shaft. The link includes a pulley portion. A first control cable that pivots the link in one direction extends out of the surgical instrument shaft and crosses the width of the instrument in a first crossing direction. The first control cable is then routed around the pulley portion of the link in a first circumferential direction. Similarly, a second control cable that pivots the link in the opposite direction extends out of the surgical instrument shaft and crosses the width of the instrument in a second crossing direction. The second control cable is then routed around the pulley portion of the link in a second circumferential direction that is opposite the first circumferential direction.

23 Claims, 5 Drawing Sheets

(56) References Cited

U.S. PATENT DOCUMENTS

2006/0030841 A1* 2/2006 Madhani et al. ................ 606/1
2006/0264787 A1 11/2006 Yamada et al.
2008/0051239 A1 2/2008 Jinno et al.

OTHER PUBLICATIONS

PCT/US09/46237 International Search Report and Written Opinion of the International Searching Authority, mailed Mar. 4, 2011, 11 pages.

* cited by examiner

SURGICAL INSTRUMENT WRIST

RELATED APPLICATIONS

This application claims the benefit of U.S. Provisional Patent App. No. 61/078,543 (filed 7 Jul. 2008) by Murphy et al., entitled "Surgical Instrument Wrist", which is incorporated herein by reference.

BACKGROUND

1. Field of Invention

Aspects of the invention pertain to surgical instruments, and more particularly to wrist mechanisms for minimally invasive instruments.

2. Art

In a telerobotic surgical system, wristed surgical end effectors on minimally invasive surgical instruments provide one or more degrees of freedom (DOFs) at a surgical site within a patient. For example, FIG. 1 is a diagrammatic view of a typical minimally invasive surgical instrument used by the da Vinci® Surgical System, manufactured by Intuitive Surgical, Inc., Sunnyvale, Calif. The instrument includes a force transmission mechanism 2 that is removably coupled to a robotic manipulator arm in the surgical system (see also FIG. 6 and the associated description below). Rotational forces from servomotor actuators in the manipulator arm engage components in transmission mechanism 2, which in turn transmits the forces to cables or cable/hypotube combinations that run through shaft 4. A surgical end effector 6 (e.g., grasper, scissors, retractor, stabilizer, cautery implement, and the like) is positioned at the distal (towards the surgical site) end of shaft 4. Wrist mechanism 8 provides DOFs for end effector 6. For reference purposes herein, locations closer to the surgical site may be referred to as distal, and locations farther from the surgical site may be referred to as proximal. Details of illustrative instrument implementations, including examples of transmission mechanisms, wrists, and end effectors, are found in, e.g., U.S. Pat. No. 6,394,998 B1 (filed Sep. 17, 1999), which is incorporated by reference. A brief summary is provided with reference to FIGS. 2A and 2B.

FIG. 2A is an illustrative diagrammatic elevation view of a portion of a wrist mechanism 8 for a minimally invasive surgical instrument. A clevis 9 (illustrated in dashed line), which may be referred to herein as a proximal clevis in the instrument, is positioned at the distal end of shaft 4. A clevis link 10 is positioned in and is held by the proximal clevis 9. Clevis link 10 includes a pulley portion 12 at a proximal end and a clevis portion 14 at a distal end. Clevis portion 14 may be referred to herein as a distal clevis in the instrument. Clevis portion 14 holds one or more pivoting members. In FIG. 2A, two jaw members 16a,16b are shown.

Two illustrative cables 18a,18b are used to move clevis link 10 with reference to shaft 4. The term "cable" is broadly used herein to mean any tendon-like component (e.g., wire, twisted wire cable, etc.). As shown in FIG. 2A, cable 18a extends through and out of the distal end of shaft 4 and is coupled to the "top" of clevis link 10. Likewise, cable 18b extends through and out of the distal end of shaft 4 and is coupled to the "bottom" of clevis link 10. Consequently, clevis link 10 pivots around axis 20 as tensile forces are alternatively applied and removed from cables 18a, 18b. The pivoting movement of clevis link 10 around axis 20, as indicated by the directional arrows, is arbitrarily referred to herein as pitch (motion into and out of the page is therefore arbitrarily referred to herein as yaw). As clevis link 10 rotates around axis 20, the cables 18a,18b wrap around the grooved circumference of pulley portion 12. As a result, a constant moment arm $r_1$ is created between axis 20 and the point on pulley portion 12 at which a cable in tension is tangent.

FIG. 2B shows an illustrative implementation of the wrist mechanism described above. FIG. 2B shows the distal end of a "Long Tip Forceps" instrument (model nos. 400048 or 420048) used with da Vinci® Surgical Systems. The proximal clevis 22 is clearly seen at the distal end of the instrument shaft, and two illustrative grasping jaws 24a,24b are shown held in distal clevis 26.

The amount of force in pitch (around axis 20) available at the distal tips 28a,28b is important for surgical tasks such as dissection and retraction in which one or both of the distal tips 28a,28b of the jaws 24a,24b are used to move or separate tissue. It can be seen that the relationship between the amount of force in pitch that the distal tips 28a,28b of the jaws 24a,24b can apply is directly related to (i) the amount of force that the cables can apply to move clevis link 26 in pitch, (ii) the length of the moment arm $r_1$ in pulley portion 12 on which the cable in tension is acting, and (iii) the distance between the distal tips 28a,28b and the pitch axis 20 defined by the proximal clevis 22. To be effective, however, certain surgical instruments require long jaws, and so the amount of force available at the distal tips of such long end effectors is reduced to a level that makes the instrument relatively ineffective for some surgical tasks.

In the wrist architecture illustrated by FIGS. 2A and 2B, the amount of force the cables can apply to clevis link 10 is limited by the physical constraints of the cables or cable/hypotube combinations in the instrument. For example, above a certain tensile force, cables may have an increased tendency to break or to unacceptably stretch.

In addition, it is difficult to lengthen the moment arm r in the wrist architecture illustrated by FIGS. 2A and 2B. The instrument (e.g., about 8 mm outer diameter) must fit through a closely fitting cannula as it extends towards a surgical site within the patient (again, see FIG. 6), which places an upper limit on $r_1$. Moreover, in the depicted wrist architecture, if $r_1$ is increased, then the cables 18a, 18b begin to rub against the outer parts of the openings 32a,32b at the end of the shaft through which they run. This rubbing results in friction and stick/slip that causes, e.g., unacceptable cable wear and or hysteresis.

What is needed, therefore, is a wrist architecture that provides an increased force in pitch at the distal tip of a surgical end effector while conforming to an outer diameter limitation for the wrist mechanism due to existing surgical system size constraints.

SUMMARY

In accordance with aspects of the invention, a link is positioned to pivot at the distal end of a surgical instrument shaft. In some aspects the link may pivot on an axis fixed at the shaft's end. The link includes a pulley portion. A first control cable that pivots the link in one pitch direction extends out of the surgical instrument shaft and around a first idler pulley that is adjacent the pulley portion of the link. The first control cable then routed across the instrument in a first crossing direction and is routed around the pulley portion of the link. Similarly, a second control cable that pivots the link in the opposite pitch direction extends out of the surgical instrument shaft and around a second idler pulley that is also adjacent the pulley portion of the link. The second control cable then extends across the width of the instrument in a second crossing direction and is routed around the pulley portion of the link. Routing the control cables across the instrument allows the pulley portion to provide a larger moment arm for the link while avoiding friction at the openings where the cables extend from the instrument shaft.

In accordance with a second aspect of the invention, the link includes a guide channel that keeps a yaw control cable for the end effector from being disengaged from an idler pulley on the link. The guide channel counteracts an increased tendency of the end effector control cable to disengage from the link idler pulley in various conditions, for example due to relatively higher tissue reactive forces on the instrument from the increased tip force available with the use of the crossing pitch control cables.

DETAILED DESCRIPTION

This description and the accompanying drawings that illustrate aspects, implementations, and embodiments of the present invention should not be taken as limiting—the claims define the protected invention. Various mechanical, compositional, structural, electrical, and operational changes may be made without departing from the spirit and scope of this description and the claims. In some instances, well-known circuits, structures, and techniques have not been shown or described in detail in order not to obscure the invention. Like numbers in two or more figures represent the same or similar elements. Drawings are not necessarily to scale.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes includes various special device positions and orientations.

In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. All examples and illustrative references are non-limiting and should not be used to limit the claims to specific implementations and embodiments described herein and their equivalents.

Figure 3:
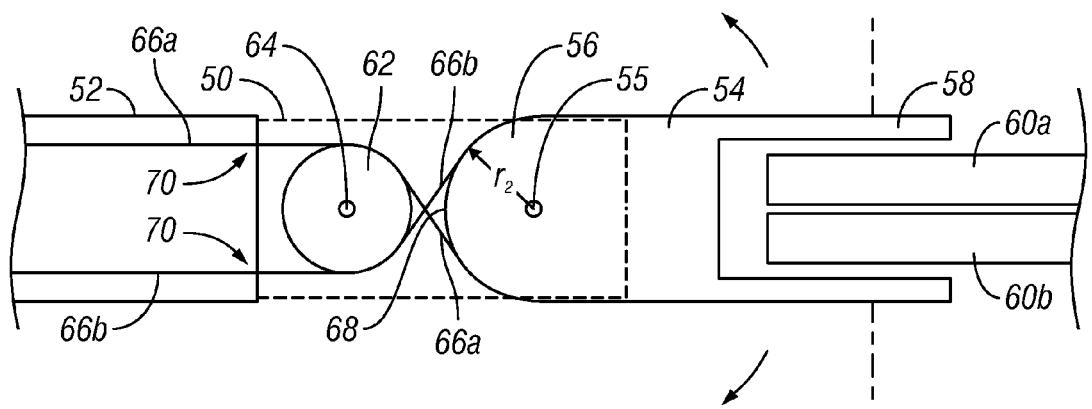
FIG. 3 is a diagrammatic elevation view of a wrist mechanism in accordance with aspects of the invention.

FIG. 3 is a diagrammatic elevation view of a wrist mechanism in accordance with aspects of the invention. A proximal clevis 50 (shown in dashed line) is positioned at the distal end of a minimally invasive surgical instrument shaft 52. A clevis link 54 is positioned to pivot in pitch (again, "pitch" is an arbitrary term herein) around axis 55 (as shown by the direction arrows) in proximal clevis 50. Clevis link 54 includes a pulley portion 56 and a distal clevis portion 58. Jaw members 60a,60b are positioned to pivot within distal clevis portion 58, and they are illustrative of one or more instrument components that serve as surgical end effectors.

FIG. 3 also shows idler pulleys 62 positioned proximal of clevis link 54. In the figure, one idler pulley is hidden behind the other. In one illustrative implementation, idler pulleys 62 are also positioned within proximal clevis 50. Idler pulleys 62 rotate around axis 64, which is generally parallel to axis 55. Each idler pulley 62 has a groove around its outer circumference, and the idler pulleys are positioned to be aligned with two corresponding grooves formed in pulley portion 56. In an alternate aspect, the length of the clevis 50 ears do not necessarily have to extend over the full diameter of the idler pulleys 62, so that the idler pulleys 62 may be positioned proximal of clevis 50 that supports clevis link 54. In these illustrative aspects, the axes 55 and 64 remain stationary with reference to the instrument shaft 52.

A first pitch control cable 66a is routed through and out the distal end of instrument shaft 52. The proximal end of pitch control cable 66a may be coupled to a transmission mechanism as described above, or it may be permanently coupled to an actuator, such as a servomotor. The distal end of pitch control cable 66a is routed in a first, clockwise direction around one of the idler pulleys 62 and then across the instrument's centerline (i.e., across the instrument's width) towards pulley portion 56 of clevis link 54. The distal end of pitch control cable 66a is then routed around the corresponding first groove in pulley portion 56 in a second, counterclockwise direction and is anchored in clevis link 54 (e.g., by a swaged cable end held in place by a fitting in the clevis link). In a similar manner, a second pitch control cable 66b is routed from shaft 52, around the second idler pulley 62 in a counterclockwise direction, width-wise across the instrument, and around the corresponding second groove in pulley portion 56 in a clockwise direction. Consequently, applying tension on cable 66a and releasing tension on cable 66b will cause clevis link 54 to pitch "down" as shown in the figure around axis 55, and similarly applying tension on cable 66b and releasing tension on cable 66a will cause clevis link 54 to pitch "up".

The wrist architecture illustrated in FIG. 3 allows the moment arm $r_2$ between axis 55 and the outer circumference 68 of pulley portion 56 to be relatively larger than moment arm $r_1$ discussed above without causing the cable rubbing problem that would result if the pulley portion of the clevis link were merely made larger. Thus the pitch control cables 66a,66b can be routed substantially straight out of the distal end of instrument shaft 52 without any significant rubbing against openings 70 (e.g., because the idler pulley diameters are about the same width as the distance between the openings), and yet the pulley portion 56 can be made to provide a moment arm $r_2$ that is close to the outer diameter size limits of the instrument.

It can be seen that the two idler pulleys need not be concentric. Smaller, non-concentric idler pulleys may used in some implementations. And, other acceptably low friction cable routing devices (e.g., fair leads, and the like) may be used instead of idler pulleys. In accordance with an aspect of the invention, after exiting the distal end of the shaft and adjacent to the pulley portion of the clevis link, the pitch control cables are routed across the instrument before being routed around the pulley portion of the clevis link, thereby allowing the moment arm provided by the pulley portion (i.e., the radius of the pulley portion) to be increased.

Figure 1:
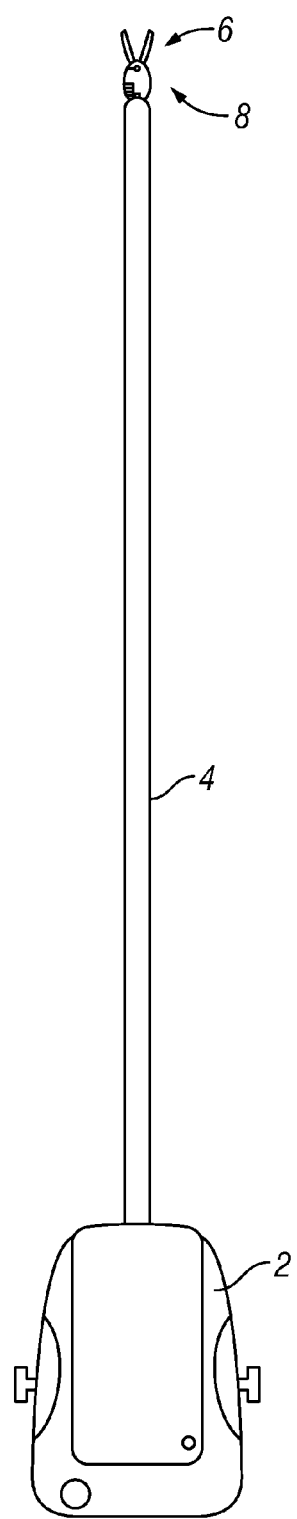
FIG. 1 is a diagrammatic view of a minimally invasive surgical instrument.
Figure 2A:
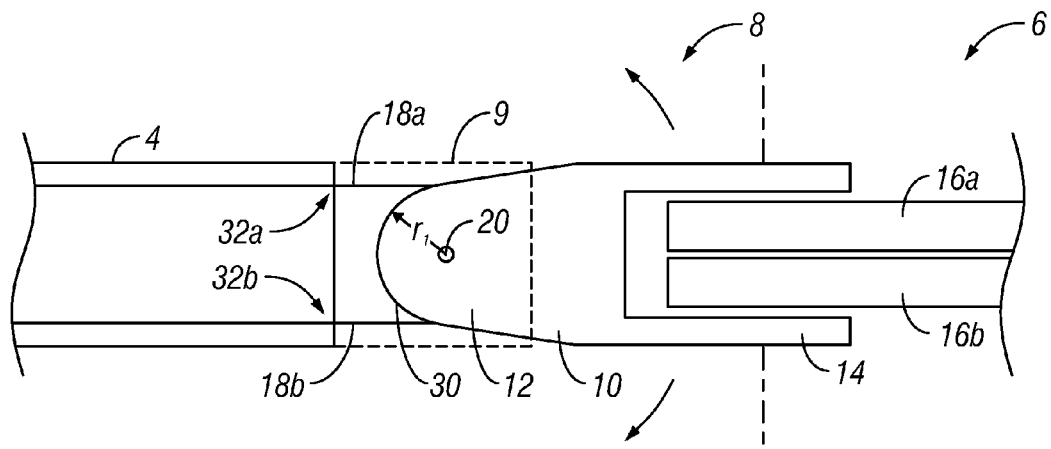
FIG. 2A is a diagrammatic elevation view of a portion of a wrist assembly for a minimally invasive surgical instrument.
Figure 2B:
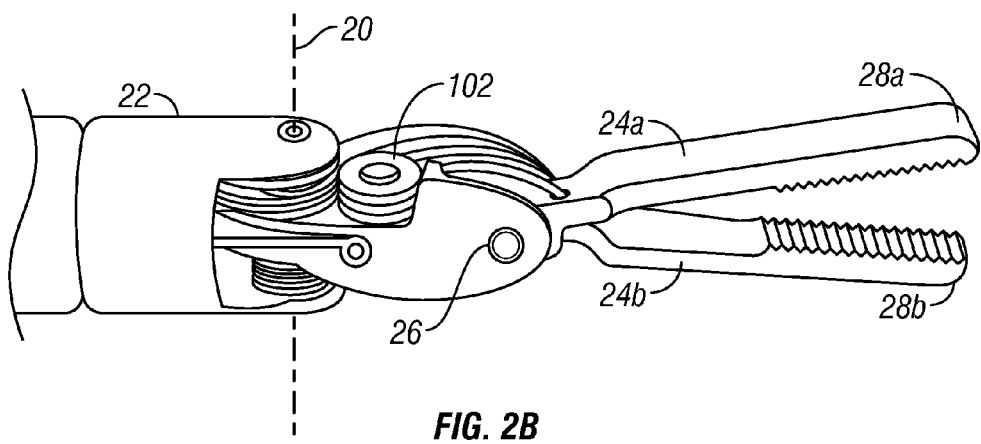
FIG. 2B illustrates an implementation of such an assembly.

In one illustrative implementation, the instrument shaft is approximately 0.329-inch OD, the idler pulleys are approximately 0.210-inch OD, the pulley portion 54 diameter is approximately 0.300-inch, and the distance between axes 55 and 64 is approximately 0.275 inches. The pulley portion diameter in this implementation compares very favorably to the 0.218-inch pulley diameter used in a comparably sized instrument with the wrist architecture described with reference to FIGS. 2A and 2B (approximately 38 percent increase in the moment arm $r_2$ versus $r_1$; the actual dimensions are slightly different due the depth of the cable grooves in the pulley portion of the clevis link). Consequently, the available force in pitch for clevis link 54 is increased (e.g., by approximately 38 percent), which allows (i) existing surgical end effectors to apply more force in pitch, and (ii) new, longer surgical end effectors to be designed with adequate force in pitch available for surgical use at the instrument tips.

Figure 4:
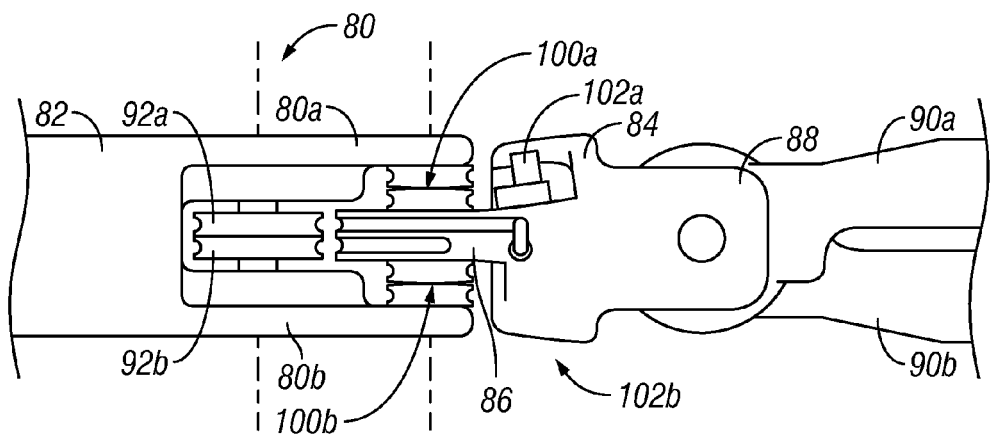
FIG. 4 is a diagrammatic plan view that shows additional details of an implementation of a wrist mechanism in accordance with aspects of the invention.

FIG. 4 is a diagrammatic plan view that shows additional details of an example wrist mechanism in accordance with aspects of the invention. Cables are omitted from FIG. 4 in order to more clearly show illustrative components. As described above, a proximal clevis 80, having two clevis ears 80a,80b, is positioned at the distal end of a shaft 82 for a minimally invasive instrument used in a telerobotic surgical system (although implementations are not limited to such surgical systems). Clevis link 84 is positioned so that pulley portion 86 pivots within proximal clevis 80. Distal clevis portion 88 of clevis link 84 holds two illustrative opposing jaw members 90a,90b. In addition, idler pulleys 92a,92b are positioned within proximal clevis 80. Circumferential cable grooves in idler pulleys 92a,92b are generally aligned with corresponding cable grooves in pulley portion 86 of clevis link 84.

From the description above it can be seen that one pitch control cable is to be routed "behind" idler pulley 92a and into the corresponding "top" cable groove in pulley portion 86 as shown in FIG. 4. The other pitch control cable is to be routed "in front of" idler pulley 92b and into the corresponding "bottom" cable groove in pulley portion 86. Swaged ends of the cables are held in fixture 94.

It should be understood that although aspects of the invention are illustrated with two separate pitch control cables, in some implementations a single cable having two lengths extending proximally from the pulley portion of the clevis link may be used. Such a single cable embodiment may anchor the cable to the clevis link in various conventional ways, including friction coupling, swage ball, etc.

FIG. 4 also illustrates two more sets 100a,100b of two idler pulleys positioned coaxially with pulley portion 86 in proximal clevis 80. These additional idler pulleys are used to route yaw/grip control cables that extend from shaft 82 to jaws 90a,90b. Such cables, and their routing, are illustratively described in U.S. Pat. No. 6,394,998 B1, incorporated by reference above. Similar idler pulleys are also shown (partially hidden, but with associated cables partly shown) mounted to rotate around axis 20 in FIG. 2B.

In addition to sets 100a,100b of idler pulleys, two additional sets of idler pulleys (not shown; see e.g., FIG. 5) are mounted on clevis link 84 to guide the yaw/grip control cables. These sets of idler pulleys are mounted on pins 102a (shown) and 102b (hidden) in the clevis link. As mentioned above, opposing cables are used to move distal components of the surgical instrument, and when tension is applied to one cable, tension is released from the opposing cable. Due to material characteristics and manufacturing tolerances, in certain circumstances the amount of slack in a released cable may exceed the path length of the cable through the wrist mechanism. If the slack is too large, for instance if the distal tip of the instrument is experiencing a large reactive force while a wrist component is at or near a limit range of motion, the slack in the released cable may be large enough to cause the cable to move out of the circumferential groove in the clevis link idler pulleys. Then, when the distal instrument component is moved towards a more neutral position, the cable may stay disengaged from the idler pulley groove, and the resulting cable slack may render the instrument unusable, or at least significantly degrade its performance.

Accordingly, in another aspect of the invention the clevis link 84 is modified with a cable guide channel that keeps the yaw/grip control cables from becoming disengaged from the idler pulleys mounted on the clevis link.

Figure 5:
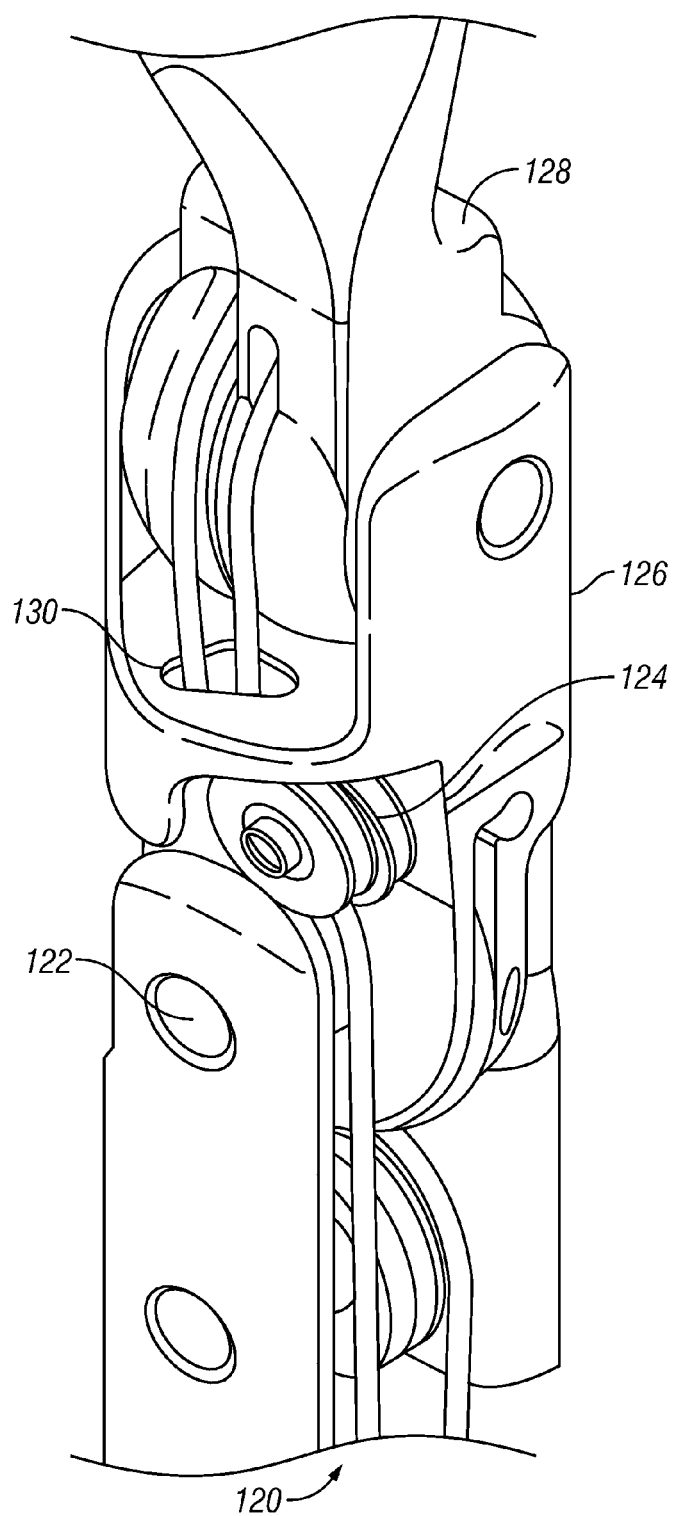
FIG. 5 is a perspective view of a wrist mechanism with cable routing on a wrist link in accordance with an aspect of the invention.

FIG. 5 is a perspective view of an illustrative wrist mechanism implementation with cable routing in accordance with an aspect of the invention. Yaw/grip control cables 120 extend from the distal end of the instrument shaft, around a first set of idler pulleys (mostly hidden from view) coaxial with the distal-most clevis pin 122 in the proximal clevis, around a second set 124 of idler pulleys mounted on clevis link 126, and to jaw members 128. The yaw/grip control cables 120 pass through guide channel 130 between the second set 124 of idler pulleys and the jaw members 128. This guide channel prevents one or both of cables 120, when slack, from moving away from a path that is aligned with the idler pulleys 124. Therefore, when tension is reapplied, the cable(s) return(s) to the proper idler pulley 124 groove.

As shown in FIG. 5, guide channel 130 is illustratively positioned at the base of the distal clevis and has a rounded triangular cross section, although other cross-sectional shapes may be used. Guide channel 130 is shaped, and positioned in the clevis link, so that the cables 120 do not rub against the walls of the guide channel when under tension. When slack, however, some contact may occur between a cable and the guide channel wall, but since the cable is slack there is no appreciable wear on the cable, and consequently instrument performance is not degraded over the expected life of the instrument (e.g., ten uses).

Figure 6:
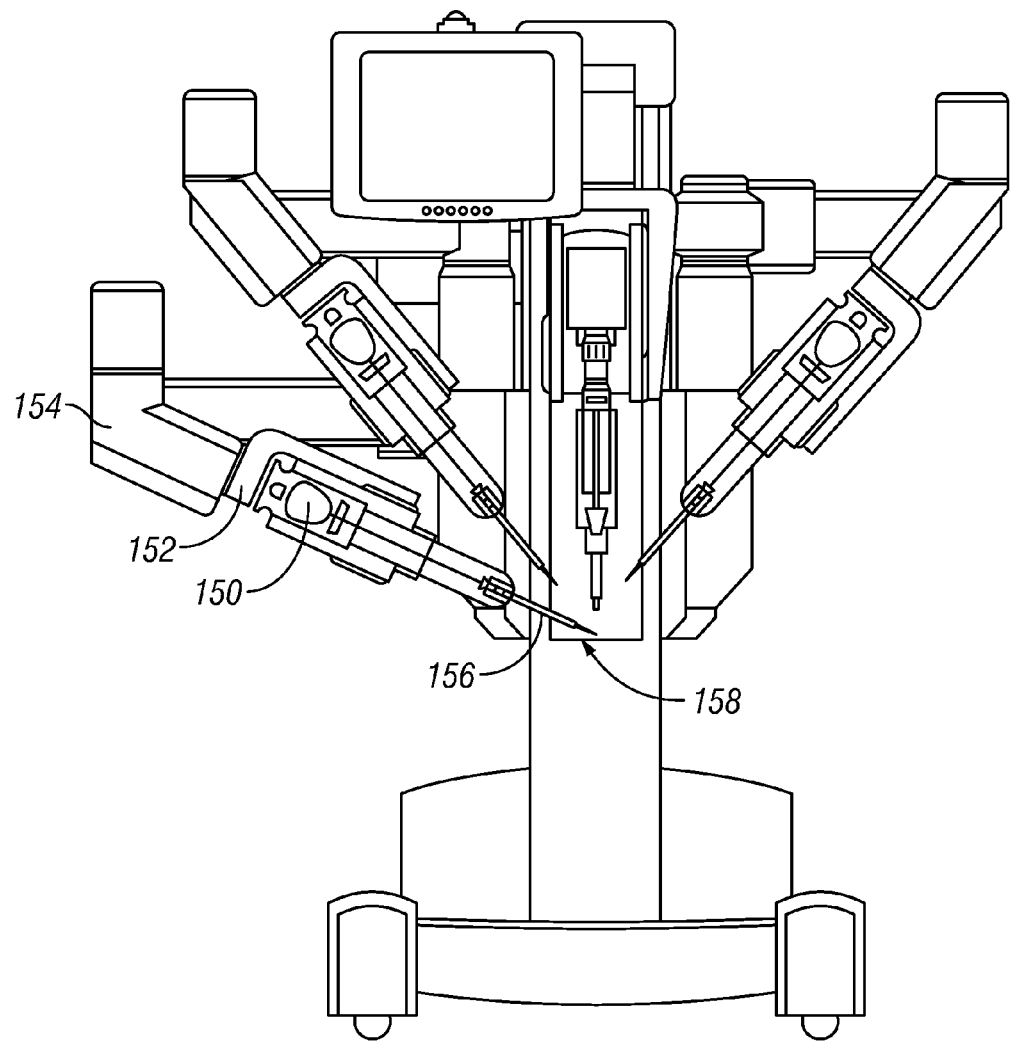
FIG. 6 is front elevation view of a portion of a telerobotic minimally invasive surgical system.

FIG. 6 is front elevation view of the "patient side cart" portion of a da Vinci® S™ HD™ Surgical System in which instruments incorporating aspects of the invention may be used. As shown in FIG. 6, for example, such an instrument 150 is removably mounted on a teleoperated robot manipulator arm 152. The manipulator arm is mounted on a passively jointed setup arm 154. When instrument 150 is mounted to manipulator arm 152, the instrument shaft extends through a cannula 156 that has been placed in a patient's body wall. Accordingly, instrument 150's distal components—e.g., a wrist implementation in accordance with aspects of the invention—must be sized to be inserted through cannula 156. As shown in FIG. 6, the cannula is removably attached to manipulator arm 152. The instrument's wristed end effector 158 is extended to work at a surgical site within the patient to work under the teleoperated control of a surgeon.

Aspects of the invention are not limited to use with such a telerobotic system. For example, aspects of the invention may be used with hand-held powered or unpowered instruments in surgical or non-surgical implementations.

What is claimed is:

1. A surgical instrument comprising:
   a shaft;
   a link including a proximal end and a distal end, the link having a fixed pulley portion on the proximal end, the link being positioned to pivot on an axis fixed at a distal end of the shaft;
   a surgical end effector coupled to the distal end of the link;
   first and second idler pulleys positioned proximally of and adjacent to the link;
   a first control cable that extends from the shaft, around the first idler pulley in a first circumferential direction, and around the fixed pulley portion of the link in a second circumferential direction that is generally opposite to the first circumferential direction; and
   a second control cable that extends from the shaft, around the second idler pulley in the second circumferential direction, and around the fixed pulley portion of the link in the first circumferential direction.

2. The surgical instrument of claim 1:
   wherein the link is mounted to pivot in a proximal clevis at the distal end of the shaft.

3. The surgical instrument of claim 1:
   wherein the link is mounted to pivot in a proximal clevis at the distal end of the shaft; and
   wherein the first and second idler pulleys are also mounted within the proximal clevis.

4. The surgical instrument of claim 1:
   wherein the first and second idler pulleys are concentrically mounted; and
   wherein the diameters of the first and second idler pulleys are approximately the distance between openings at the distal end of the shaft through which the first and second control cables extend.

5. The instrument of claim 1:
   wherein the first and second control cables are each portions of a single cable.

6. The instrument of claim 1:
   wherein the link comprises a distal clevis; and
   wherein the surgical end effector is mounted to pivot in the distal clevis.

7. The instrument of claim 1 further comprising:
   a yaw control cable; and
   a link idler pulley mounted on the link;
   wherein the link comprises a distal clevis and a guide channel;
   wherein the surgical end effector is mounted to pivot in the distal clevis; and
   wherein the yaw control cable extends from the distal end of the shaft, around the link idler pulley, through the guide channel, and is coupled to the surgical end effector, the guide channel being positioned to prevent the yaw control cable from becoming disengaged from the link idler pulley.

8. A surgical instrument comprising:
   a shaft;
   a link including a proximal end and a distal end, the link having a fixed pulley portion on the proximal end, the link being positioned to pivot on an axis fixed at a distal end of the shaft;
   a surgical end effector coupled to the distal end of the link;
   a first control cable that extends from the shaft, across a width of the instrument in a first crossing direction adjacent the fixed pulley portion of the link, and around the fixed pulley portion of the link in a first circumferential direction; and
   a second control cable that extends from the shaft, across the width of the instrument in a second crossing direction adjacent the fixed pulley portion of the link, and around the fixed pulley portion of the link in a second circumferential direction that is opposite the first circumferential direction.

9. The surgical instrument of claim 8:
   wherein the link is mounted to pivot in a proximal clevis at the distal end of the shaft.

10. The instrument of claim 8 further comprising:
    first and second idler pulleys;
    wherein the first control cable is routed around the first idler pulley to extend across the width of the instrument; and
    wherein the second control cable is routed around the second idler pulley to extend across the width of the instrument.

11. The surgical instrument of claim 10:
    wherein the link is mounted to pivot in a proximal clevis at the distal end of the shaft; and
    wherein the first and second idler pulleys are also mounted within the proximal clevis.

12. The surgical instrument of claim 10:
    wherein the first and second idler pulleys are concentrically mounted; and
    wherein the diameters of the first and second idler pulleys are approximately the distance between openings at the distal end of the shaft through which the first and second control cables extend.

13. The instrument of claim 8:
    wherein the first and second control cables are each portions of a single cable.

14. The instrument of claim 8:
    wherein the link comprises a distal clevis; and
    wherein the surgical end effector is mounted to pivot in the distal clevis.

15. The instrument of claim 8 further comprising:
    a yaw control cable; and
    a link idler pulley mounted on the link;
    wherein the link comprises a distal clevis and a guide channel;
    wherein the surgical end effector is mounted to pivot in the distal clevis; and
    wherein the yaw control cable extends from the distal end of the shaft, around the link idler pulley, through the guide channel, and is coupled to the surgical end effector, the guide channel being positioned to prevent the yaw control cable from becoming disengaged from the link idler pulley.

16. A method of assembling a surgical instrument, comprising:
    positioning a link to pivot on an axis fixed at a distal end of an instrument shaft, the link having a proximal end and a distal end, the link including a fixed pulley portion on the proximal end;
    coupling a surgical end effector to the link;
    routing a first control cable from the instrument shaft, across a width of the instrument in a first crossing direction adjacent the fixed pulley portion of the link, and around the fixed pulley portion of the link in a first circumferential direction; and routing a second control cable from the instrument shaft, across the width of the instrument in a second crossing direction adjacent the fixed pulley portion of the link, and around the fixed pulley portion of the link in a second circumferential direction that is opposite the first circumferential direction.

17. The method of claim 16:
wherein coupling the surgical end effector to the link comprises positioning the surgical end effector to pivot in a distal clevis of the link.

18. The method of claim 16:
wherein routing the first control cable across the width of the instrument comprises routing the first control cable around a first idler pulley in the second circumferential direction; and
wherein routing the second control cable across the width of the instrument comprises routing the second control cable around a second idler pulley in the first circumferential direction.

19. The method of claim 16 further comprising:
positioning first and second idler pulleys in a proximal clevis at the distal end of the instrument;
wherein positioning the link to pivot at a distal end of an instrument shaft comprises positioning the link in the proximal clevis;
wherein routing the first control cable across the width of the instrument comprises routing the first control cable around the first idler pulley in the second circumferential direction; and
wherein routing the second control cable across the width of the instrument comprises routing the second control cable around the second idler pulley in the first circumferential direction.

20. The method of claim 16 further comprising:
routing a yaw control cable from the instrument shaft, around a link idler pulley on the link, through a guide channel in the link, and to the surgical end effector;
wherein the guide channel is positioned to prevent the yaw control cable from becoming disengaged from the link idler pulley.

21. The surgical instrument of claim 1, wherein an axis of rotation of the first and second idler pulleys is parallel to the pivot axis of the link.

22. The surgical instrument of claim 1, wherein an axis of rotation of the surgical end effector is perpendicular to the pivot axis of the link.

23. The surgical instrument of claim 8, wherein an axis of rotation of the surgical end effector is perpendicular to the pivot axis of the link.

\* \* \* \* \*